United States Patent [19]

Ferrand et al.

[11] Patent Number: 4,649,153

[45] Date of Patent: Mar. 10, 1987

[54] 5,6-DIHYDRO-4H-CYCLOPENTA(B)THIOPHENE-6-CARBOXYLIC ACIDS, PREPARATION PROCESSES AND MEDICINES CONTAINING THEM

[75] Inventors: Gérard Ferrand, Lyon; Jacques Barbanton, Brignais; Jean-Claude Depin, Lyon, all of France

[73] Assignee: Lipha, Lyonnaise Industrielle Pharmaceutique, Lyon, France

[21] Appl. No.: 746,785

[22] Filed: Jun. 20, 1985

[30] Foreign Application Priority Data

Jul. 9, 1984 [FR] France ............................. 84 10861

[51] Int. Cl.$^4$ ..................... A61K 31/38; C07D 333/56
[52] U.S. Cl. ......................................... 514/443; 549/57
[58] Field of Search ........................... 549/57; 514/443

[56] References Cited

FOREIGN PATENT DOCUMENTS 487841 of 0000 Spain .

*Primary Examiner*—Alan Siegel
*Attorney, Agent, or Firm*—Browdy and Neimark

[57] ABSTRACT

5,6-dihydro-4H-cyclopenta[b]thiophene-6-carboxylic acids represented by the formula:

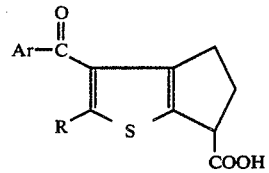

in which Ar is a phenyl or thienyl group, optionally substituted, or a furyl group; R is a lower alkyl radical, are useful as anti-inflammatory and analgesic medicines.

11 Claims, No Drawings

5,6-DIHYDRO-4H-CYCLOPENTA(B)THIOPHENE-6-CARBOXYLIC ACIDS, PREPARATION PROCESSES AND MEDICINES CONTAINING THEM

FIELD OF THE INVENTION

This invention relates to 3-aroyl-5,6-dihydro-4H-cyclopenta[b]thiophene-6-carboxylic acids, and esters, amides and salts thereof, processes making them and their application in the therapeutic field.

BACKGROUND OF THE INVENTION

Many non-steroid anti-inflammatory products have been discovered in the last twenty years. However, the search continues for compounds that are more effective and better tolerated in comparison with present products and their development remains a major objective of therapeutic research.

A. Ermili and L. Salamon have described some 5,6-dihydro-6-alkyl-2-aryl-4H-cyclopenta[b]thiophene-5-carboxylic acids and 5,6-dihydro-6-alkyl-2-aryl-4H-cyclopenta[b]thiophene-4-carboxylic acids [Ann. Chim. (Rome) 1969, 59, 375]. German patent No. 2,443,086 has as its object 2-aryl-3-hydroxy or alkoxy-5,6-dihydro-4H-cyclopenta[b]thiophene-4-carboxylic acids. Mention is made in Spanish Pat. No. 468,064 of 5,6-dihydro-4H-cyclopenta[b]thiophene-4-carboxylic acid. 5,6-Dihydro-4H-cyclopenta[b]thiophene-4-carboxylic acids able to carry a benzoyl group in the 2 or 3 position were presented as anti-inflammatory agents in Spanish Pat. No. 487,841, the preferred product being 2-isobutyl-5,6-dihydro-4H-cyclopenta[b]thiophene-4-carboxylic acid. Finally, the preparation of 5-ethyl-5,6-dihydro-4H-cyclopenta[b]thiophene-6-carboxylic acid appears in Spanish Pat. No. 468,129.

SUMMARY OF THE INVENTION

A new series of very effective and well tolerated compounds, able to be used in the treatment of inflammation, pain and pyrexia, has now been found.

The acid compounds of this invention are shown by general formula I

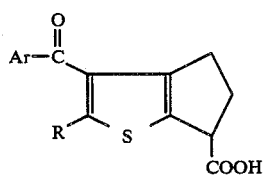

in which Ar is a phenyl or thienyl group, optionally substituted, or a furyl group; R is a lower alkyl radical, preferably of $C_1$–$C_3$.

When Ar represents a phenyl group, the substituent or substituents can occupy any position and can be a halogen atom, a lower alkyl, lower alkoxy, hydroxy, nitro or dimethylamino group. When Ar represents thienyl or furyl groups, these can be linked to the rest of the molecule by their 2 or 3 summit. The thiophene ring can be substituted by a lower alkyl group or a halogen atom. The term "lower" applied to an alkyl or alkoxy group signifies that the group can be linear or branched and that it can comprise from 1 to 6 carbon atoms.

Pharmaceutically acceptable salts and the compounds that derive from the conversion of the carboxyl group such as esters or amides are an integral part of the invention.

DETAILED DESCRIPTION OF EMBODIMENTS

The salts can be salts of alkali metals such as sodium or potassium, of alkaline earth metals such as calcium or magnesium or metals such as aluminum. They can be ammonium salts or salts deriving from organic bases such as mono-, di-, or tri-alkylamines of low molecular weight, ethanolamine, tromethamine, lysine, arginine or glucosamine.

The derivatives of the acids of formula I can be esters such as aliphatic, aryl, benzyl esters, amino esters such as dialkylaminoalkyl esters, amides such as carboxamides optionally substituted on the nitrogen atom.

The compounds answering to formula I and their ester or amide derivatives having an asymmetric carbon exist in the form of pairs of optical isomers. Each optical isomer and their mixture are part of the invention. The optical isomers can be separated by resolution with optical active bases such as brucine, cinchonidine or strychnine.

The compounds of the invention with the exception of those for which Ar is a phenyl ring substituted by a dimethylamino group, are obtained according to the following reactions:

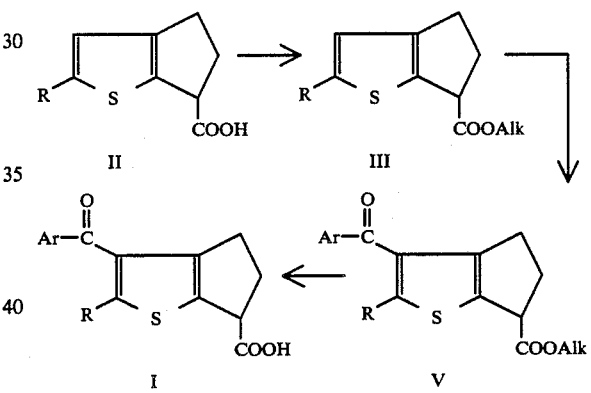

in which R and Ar have the meanings given above.

In a first stage, a 2-alkyl-5,6-dihydro-4H-cyclopenta[b]thiophene-6-carboxylic acid of general formula II is esterified to lead to the derivative of formula III in which Alk represents an alkyl group of low molecular weight, preferably the methyl or ethyl group. The reaction is performed according to standard techniques, for example by treating acids II with methanol or ethanol in the presence of an acid catalyst such as sulfuric acid, hydrochloric acid or paratoluenesulfonic acid.

Esters III are then treated with an aroyl halide of general formula IV $$Ar-CO-X \qquad IV$$

X designating a halogen atom, to lead to the derivatives of general formula V. This Friedel-Crafts type reaction can be performed with or without solvent, but preferably with solvent, in the presence of a Lewis catalyst. The solvents most suitable for performing this reaction are methylene chloride, 1,2-dichloroethane, tetrachloroethane, chlorobenzene, dichlorobenzene, carbon disulfide or nitrobenzene. The Lewis catalysts used are those traditionally used in this type of reaction. Thus, there can be mentioned aluminum chloride, aluminum bromide, titanium chloride, iron chloride, tin chloride, boron chloride. Aluminum chloride is a particularly preferred catalyst.

The reagents used can be in stoichiometric amount or in excess. It is often advantageous to operate with an excess of aroyl halide that can go up to 200% and with an excess of catalyst that can go up to 400%. The reaction temperature is between ambient temperature and the boiling temperature of the solvent used. The reaction time can vary from 1 hour to 12 hours. Depending on the case, it is possible either to add catalyst to a solution of aroyl chloride and ester III or to add the aroyl chloride to a mixture of catalyst and ester III in the solvent chosen.

When Ar is a phenyl ring substituted in the ortho position by a methoxy group, during the Friedel-Crafts reaction an ether cleavage is produced leading to a corresponding hydroxyl analogue which must then be etherified by methyl iodide. It is then advantageous to operate in a ketone solvent such as acetone or methyl ethyl ketone in the presence of an alkaline carbonate.

The esters V are finally hydrolyzed into acids I. This hydrolysis can be performed either in an acid medium with inorganic acids such as hydrochloric acid or sulfuric acid or preferably in an alkaline medium. The bases used are hydroxides or carbonates of alkali metals, for example, sodium or potassium, hydroxide, sodium carbonate, potassium carbonate. The reaction is performed in solution in a mixture of water and low molecular weight alcohol such as methanol or ethanol, at a temperature between ambient temperature and reflux temperature, for a period between 1 hour and 12 hours. Preferably, this hydrolysis is performed by using sodium or potassium carbonate in aqueous ethanol with reflux.

The compounds of formula I for which Ar is a phenyl ring substituted by a dimethylamino group can be prepared according to the series of reactions below, in which R and Alk have the meanings given above:

Catalytic hydrogenation, in the presence of formaldehyde, of the esters of formula Va provide the derivatives of formula Vb. The preferred catalyst is Raney nickel. Good results have been obtained by operating with an aqueous solution of formaldehyde and in the presence of a catalytic amount of propionic acid. The esters Vb are then hydrolyzed according to the general method described for the passing of esters of general formula V to acids of formula I.

2-Alkyl-5,6-dihydro-4H-cyclopenta[b]thiophene-6-carboxylic acids of general formula II can be obtained in the following way.

(a) A 5-alkyl-2-thiophenecarboxaldehyde of formula VI:

in which R represents a lower alkyl group, is treated with an alkyl malonate of formula VII

in which R1 represents a low molecular weight alkyl group, preferably the methyl or ethyl group, to lead to diesters of general formula VIII

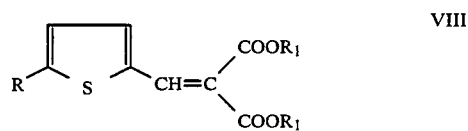

The reaction is performed with azeotropic elimination of water in the presence of acetic acid and piperidine, according to the technique described by C. F. H. Allen and F. W. Spangler [*Organic Syntheses*, Coll. Vol. III, 377].

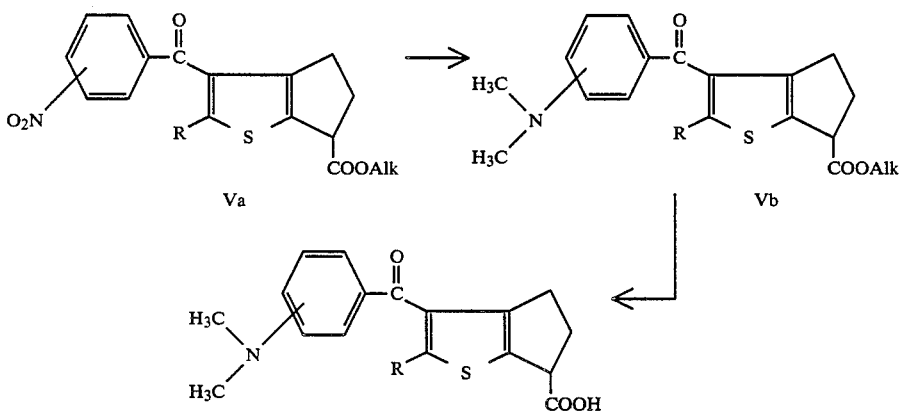

(b) Diesters VIII are transformed into succinic acids IX according to the following reaction sequence:

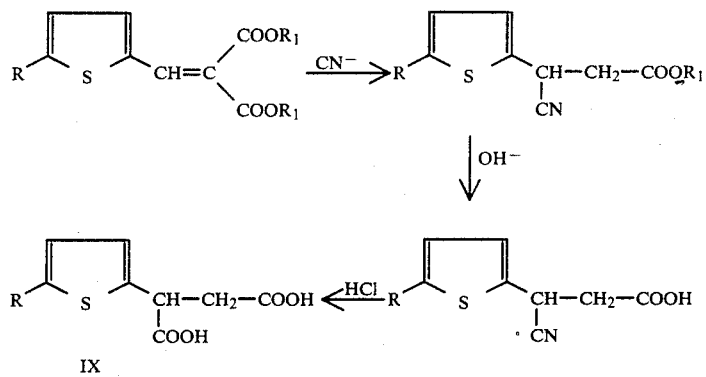

Synthesis of substituted succinic acids by this method is performed according to C. F. H. Allen and H. B. Johnson, *Organic Syntheses*, Coll. Vol. IV, 804 and K. Petterson, *Arkiv for Kemi* 1954, 7, 39. The operational details are given in the experimental part.

(c) Succinic acids IX are cyclized to give compounds of general formula X:

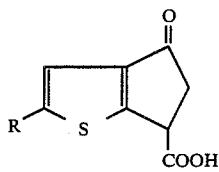

This ring formation can be used in several different ways. According to one method, diacid IX can be heated in a mixture of polyphosphoric acid and an inert solvent. The preferred solvents are aromatic hydrocarbons such as benzene, toluene, xylene. The reaction is performed at a temperature between 60° C. and the boiling temperature of the solvent used. The reaction time is between 30 minutes and 5 hours. Good results were obtained by operating in xylene at 100° C. Another preferred method consists in operating in two stages. Diacid IX is first cyclized into anhydride XI:

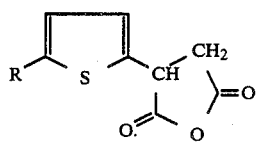

The ring formation is performed, for example, by heating diacid IX in acetic anhydride or preferably acetyl chloride. In a second stage, anhydride XI is cyclized by operating under Friedel-Crafts conditions, i.e., in the presence of a Lewis acid as catalyst. The Lewis acids used are, for example, aluminum chloride, aluminum bromide, titanium chloride, tin chloride, boron chloride. The most suitable solvents are halogenated hydrocarbons, carbon disulfide, dimethylformamide or nitrobenzene. Particularly advantageous results were obtained by using aluminum chloride and operating in nitrobenzene.

The reaction temperature is between ambient temperature and the boiling temperature of the solvent used. The reaction time can vary from 15 minutes to 5 hours.

(d) Keto-acids X are then reduced to 2-alkyl-5,6-dihydro-4H-cyclopenta[b]thiophene-6-carboxylic acids of general formula II. This Clemmensen type reduction is performed with zinc amalgam in an acid medium. The details are given in the experimental part. The esters and amides deriving from the conversion of the carboxyl group of the products of the invention are prepared in the usual way. Thus the esters can be obtained by treatment of acids I with alcohol in the presence of an acid catalyst or a halide in the presence of a base. The amides can be prepared by treatment of acids I with a halogenating agent such as thionyl chloride then reaction of resulting acid chloride with an amine.

The compounds of the invention represented by general formula I have remarkable analgesic and anti-inflammatory properties which make them useful in human medicine.

The analgesic activity was determined in rats by the Randall and Selitto method (Arch. Int. Pharmacodyn. 1957, 111, 409). Young males rats grouped by lots of 10 were treated orally with the test products in 10% gummy solution, 1 hour and immediately before subplantar injection of 0.1 ml of brewer's yeast in suspension in 20% apyrogenic physiological serum. The analgesia was evaluated 3 hours after injection of the brewer's yeast by exerting a regularly increasing pressure on the surface of the edematized paw and noting the threshold value causing a pain reaction in the animals. The dose raising the pain threshold 50% (ED 50) was calculated for each product tested.

The anti-inflammatory activity was determined by the carrageenan edema test according to Winter et al. (Proc. Soc. Exp. Biol. Med. 1962, 111, 544). Edema of a back paw was caused in male rats by subplantar injection of a 1% suspension of carrageenan in apyrogenic physiological solute. Measurement of the edema by plethysmography occurred 3 hours later. The products studied were administered orally 1 hour before the carrageenan injection. The protection conferred by the treatment was determined by calculation of ED 30 (dose moderating the edema 30% in relation to untreated animals).

The protective activity in regard to early inflammation was determined on guinea pigs according to the Winter et al. method (Arch. Int. Pharmacodyn. 1958, 116, 261). White guinea pigs having their backs freshly depilated were radiated individually by exposure to the radiation of a UV lamp placed 25 cm above the animal's back for 1 min 30 sec. The zone to be radiated was delimited by a covering pierced with circular holes wrapping each animal. The erythema was visually marked 2 hours after exposure to radiation. The guinea pigs were treated orally with the test products 1 hour after exposure to UV. The dose reducing the intensity of the erythema 50% (ED 50) for each product was sought.

Table I shows the results obtained in each of the above tests for some products of the invention and those obtained for indomethacin [1-(4-chlorobenzoyl)-5-methoxy-2-methyl-3-indolylacetic acid] taken as the standard.

of Indomethacin, is considerably greater than that of 5,6-dihydro-4H-cyclopenta[b]thiophene-4-carboxylic isomeric acids, as table II shows in which are given the results obtained in carrageenan edema, UV protection and Randall and Selitto tests for some of these acids, for the product of example 7 of this invention and for its isomer 3-benzoyl-2-methyl-5,6-dihydro-4H-cyclopenta[b]thiophene-4-carboxylic acid.

TABLE II

| Product | Formula | Carrageenan edema ED 30 (mg/kg) | Protection from UV ED 50 (mg/kg) | Randall and Selitto ED 50 (mg/kg) |
|---|---|---|---|---|
| 2-Benzoyl-5,6-dihydro-4H—cyclopenta[b]thiophene-4-carboxylic acid | | >30 | >50 | >2 × 50 |
| 2-Isobutyl-5,6-dihydro-4H—cyclopenta[b]thiophene-4-carboxylic acid | | >30 | >50 | >2 × 50 |
| 3-Benzoyl-2-isobutyl-5,6-dihydro-4H—cyclopenta[b]thiophene-4-carboxylic acid | | >30 | >50 | >2 × 50 |
| 3-Benzoyl-2-methyl-5,6-dihydro-4H—cyclopenta[b]thiophene-4-carboxylic acid | | >30 | >50 | >2 × 50 |
| 3-Benzoyl-2-methyl-5,6-dihydro-4H—cyclopenta[b]thiophene-6-carboxylic acid (Example 7) | | 0.7 | 0.4 | 2 × 0.7 |

TABLE I

| Products | Carrageenan edema ED 30 (mg/kg) | Protection from UV ED 50 (mg/kg) | Randall-Selitto ED 50 (mg/kg) |
|---|---|---|---|
| INDOMETHACIN | 5 | 4.5 | 2 × 4 |
| Example 7 | 0.7 | 0.4 | 2 × 0.7 |
| Example 10 | 3 | 0.2 | 2 × 8 |
| Example 21 | 2.4 | 0.4 | 2 × 0.5 |
| Example 27 | 1.3 | 0.6 | 2 × 0.6 |
| Example 32 | >50 | >50 | >2 × 50 |
| Example 38 | 6 | 2 | 2 × .5 |

The product described in example 7 of this invention (3-benzoyl-2-methyl-5,6-dihydro-4H-cyclopenta[b]thiophene-6-carboxylic acid) therefore shows particularly advantageous properties. Its activity, greater than that The products of the invention exhibit only a slight toxicity. Lethal doses 50 (LD50) were determined by oral administration in Swiss mice. Mortality was recorded 2 weeks later. The results obtained for some of the most active derivatives are given in Table III.

TABLE III

| Product | LD$_{50}$ P.O. (mg/kg) |
|---|---|
| INDOMETHACIN | 25 |
| Example 7 | 275 |
| Example 10 | 275 |

The medicines of the invention containing as active ingredient a compound of formula I as an anti-inflammatory, analgesic and antipyretic agent can be administered orally in the form of tablets, sugar-coated tablets or capsules, or rectally in the form of suppositories. The active agent is associated with various conventional pharmaceutically compatible excipients. Daily dosages can vary from 1 to 100 mg of active agent, depending on the age of the patient and the seriousness of the diseases treated. Some pharmaceutical formulations, by way of nonlimiting example, are given below:

| Composition of a 100-mg tablet, optionally coated: | |
|---|---|
| active agent | 5 mg |
| lactose | 41 mg |
| wheat starch | 41 mg |
| gelatin | 2 mg |
| alginic acid | 5 mg |
| talc | 5 mg |
| magnesium stearate | 1 mg |
| Composition of a capsule: | |
| active agent | 10 mg |
| lactose | 34 mg |
| wheat starch | 25 mg |
| talc | 2.5 mg |
| magnesium stearate | 0.5 mg |
| Composition of a 3 g suppository: | |
| active agent | 10 mg |
| semisynthetic triglycerides q.s.p. | 3 g |

The following examples illustrate the invention in a nonlimiting way. In the data on nuclear magnetic resonance (NMR), the following abbreviations have been used: s for singlet, d for doublet, t for triplet and m for multiplet.

EXAMPLE 1

(5-methyl-2-thienyl) succinic acid (a) Diethyl (5-methyl-2-thienyl) methylene malonate: ($C_{13}H_{16}O_4S$)

219 g (1.37 mole) of ethyl malonate was added to a mixture of 135 g (1.07 mole) of 5-methyl-2-thiophenecarboxaldehyde, 33 cc of acetic acid, 33 cc of piperidine and 1150 cc of benzene. The reaction medium was refluxed for 5 hours, while eliminating all the resulting water with a Dean-Stark apparatus, then it was concentrated under reduced pressure. The residue was picked up with methylene chloride. The organic phase was washed with water, dried on sodium sulfate and concentrated. Distillation of the excess ethyl malonate provided 263.6 g (yield: 91.5%) of diethyl (5-methyl-2-thienyl) methylene malonate in the form of a yellow solid residue used afterwards without further purification. An analytical sample could be obtained by recrystallization in pentane. Mp=60°-62° C.

| Analysis in percent | C % | H % | S % |
|---|---|---|---|
| Calculated | 58.18 | 6.01 | 11.95 |
| Found | 58.36 | 6.11 | 11.74 |

IR $\nu(C=O)=1715$ cm$^{-1}$.
NMR (CDCl$_3$) $\delta=1.2$-1.6 (m, 6H); 2.5 (s, 3H); 4.1-4.6 (m, 4H); 6.8 (d, 1H); 7.2 (d, 1H); 7.7 (s, 1H).

(b) (5-methyl-2-thienyl) succinic acid: ($C_9H_{10}O_4S$)

A solution of 120.8 g (1.86 mole) of potassium cyanide in 800 cc of water was added to a solution of 255.3 g (0.95 mole) of diethyl-(5-methyl-2-thienyl) methylene malonate in 4 liters of ethanol. The mixture was refluxed for 3 hours. Then a solution of 45 g (1.13 mole) of sodium hydroxide in 800 cc of water was added and refluxed for 1 hour. The ethanol was eliminated by distillation while keeping the volume of the reaction medium constant by simultaneous addition of water. After cooling to 40° C., hydrochloric acid was added to pH 1 and again refluxed for 1 hour. After returning to ambient temperature, the precipitate was filtered, washed with water and dried. 161.8 g (yield: 79.5%) of (5-methyl-2-thienyl) succinic acid was obtained in the form of a solid melting at 180°-182° C., used afterwards without further purification. An analytical sample was obtained by recrystallization in a hexane-ethyl acetate mixture. Mp=186°-188° C.

| Analysis in percent | C % | H % | S % |
|---|---|---|---|
| Calculated | 50.45 | 4.71 | 14.97 |
| Found | 50.64 | 4.67 | 14.66 |

IR $\nu(C=O)=1710$ and 1685 cm$^{-1}$.
NMR (CDCl$_3$) $\delta=2.3$-3.4 (m, 5H); 4.0-4.4 (m, 1H); 6.6 (d, 1H); 6.8 (d, 1H).

EXAMPLE 2

2-methyl-4-oxo-5,6-dihydro-4H-cyclopenta[b]thiophene-6-carboxylic acid: ($C_9H_8O_3S$)

23.5 g of (5-methyl-2-thienyl) succinic acid was added to a mixture of 1.2 kg of polyphosphoric acid and 200 cc of xylene, previously heated to 100° C., and stirred for 3 hours at this temperature. After cooling to 80° C. the reaction mixture was poured in 4 liters of water and extracted with ethyl acetate. The organic phase was washed with water, dried on sodium sulfate then concentrated under reduced pressure. The residue was chromatographed on a silica column (successive eluants: 1/1 hexane-ethyl acetate, then 9/0.9/0.1 methylene chloride-ethanol-acetic acid). 5.7 g (yield: 26%) of 2-methyl-4oxo-5,6-dihydro-4H-cyclopenta[b]thiophene-6-carboxylic acid was obtained which was purified by recrystallization in a hexane-ethyl acetate mixture. Mp=140°-143° C.

| Analysis in percent | C % | H % | S % |
|---|---|---|---|
| Calculated | 55.09 | 4.11 | 16.34 |
| Found | 54.90 | 3.98 | 16.09 |

IR $\nu(C=O)=1720$ and 1660 cm$^{-1}$.
NMR (CDCl$_3$) $\delta=2.5$ (s, 3H); 3.1-3.4 (m, 2H); 4.2-4.5 (m, 1H), 6.8 (s, 1H); 9.8-10.3 (broadened peak, 1H, exchangeable by CF$_3$COOD).

EXAMPLE 3

2-methyl-4-oxo-5,6-dihydro-4H-cyclopenta[b]thiophene-6-carboxylic acid (a) (5-methyl-2-thienyl) succinic anhydride: ($C_9H_8O_3S$)

15.8 g of (5-methyl-2-thienyl) succinic acid was added to 75 cc of acetyl chloride and the mixture was refluxed for 1 hour 30 minutes. The excess acetyl chloride was evaporated under reduced pressure. Bidistillation of the residue provided 10 g (yield=69%) of (5-methyl-2-thienyl) succinic anhydride. Bp1=155°-160° C.

| Analysis in percent | C % | H % | S % |
|---|---|---|---|
| Calculated | 55.09 | 4.11 | 16.34 |

-continued

| Analysis in percent | C % | H % | S % |
|---|---|---|---|
| Found | 54.95 | 4.21 | 16.12 |

IR $\nu(C=O)$: 1785 and 1870 cm$^{-1}$ (b)
2-methyl-4-oxo-5,6-dihydro-4-H-cyclopenta[b]thiophene-6-carboxylic acid 21.1 g (0.16 mole) of aluminum chloride was quickly added to 50 cc of nitrobenzene at ambient temperature. Then a solution of 11.3 g (0.058 mole) of (5-methyl-2-thienyl) succinic anhydride in 30 cc of nitrobenzene was added drop by drop in 1 hour 30 minutes. The mixture was stirred for 5 hours at ambient temperature then poured into an ice-hydrochloric acid mixture and extracted with methylene chloride. The organic phase was separated and extracted with an aqueous solution of sodium carbonate. The aqueous phase was acidified with dilute hydrochloric acid then extracted with ethyl acetate. The organic solution was washed with water, dried on sodium sulfate and concentrated under reduced pressure. 7.7 g (yield=68%) of 2-methyl-4-oxo-5,6-dihydro-4H-cyclo-penta[b]thiophene-6-carboxylic acid melting at 137°–139° C. was obtained. By recrystallization in a hexane-ethyl acetate mixture, a product was obtained with a melting point of 140°–143° C. identical in all respects with that obtained in example 2.

EXAMPLE 4

2-Methyl-4-oxo-5,6-dihydro-4H-cyclopenta[b]thiophene-6-carboxylic acid

A solution of 11.3 g (0.058 mole) of (5-methyl-2-thienyl) succinic anhydride in 30 cc of methylene chloride was added drop by drop to a mixture of 21.1 g (0.16 mole) of aluminum chloride and 50 cc of methylene chloride cooled to 0° C. The reaction mixture was stirred 5 hours at ambient temperature then poured into an ice-hydrochloric acid mixture and extracted with methylene chloride. The organic phase was separated then extracted with an aqueous sodium bicarbonate solution. The aqueous phase was acidified then, after filtration of an insoluble, again extracted with ethyl acetate. The organic extract was washed, dried on sodium sulfate and concentrated dry under reduced pressure. Recrystallization of the residue provided 3.2 g (yield=28%) of 2-methyl-4-oxo-5,6-dihydro-4H-cyclopenta[b]thiophene-6-carboxylic acid (mp=140°–143° C.) identical in all respects to that obtained in example 2.

EXAMPLE 5

2-Methyl-5,6-dihydro-4H-cyclopenta[b]thiophene-6-carboxylic acid ($C_9H_{10}O_2S$)

6.5 cc of acetic acid was added to a suspension of 64.1 g (0.98 g at) of zinc powder and 6.4 g (0.024 mole) of mercuric chloride in 65 cc of water and the mixture was stirred for 30 min. Then a solution of 14 g (0.076 mole) of 2-methyl-4-oxo-5,6-dihydro-4H-cyclopenta[b]thiophene-6-carboxylic acid in 140 cc of toluene, then 60 cc of 10N hydrochloric acid were successively added. The mixture was refluxed for 5 hours then decanted after cooling to ambient temperature. The organic phase was separated. The aqueous phase was extracted with toluene. The organic solutions were collected, washed with water and dried on sodium sulfate. Evaporation of the solvent under reduced pressure provided 9.8 g (yield=71%) of 2-methyl-5,6-dihydro-4H-cyclo-penta[b]thiophene-6-carboxylic acid (mp=105°–107° C.) which was used afterwards without further purification. An analytical sample was obtained by recrystallization in a hexane-ethyl acetate mixture. Mp=107°–109° C.

| Analysis in percent | C % | H % | S % |
|---|---|---|---|
| Calculated | 59.31 | 5.53 | 17.59 |
| Found | 59.30 | 5.46 | 17.41 |

IR $\nu(C=O) = 1700$ cm$^{-1}$.

NMR (CDCl$_3$) $\delta = 2.5$ (s, 3H); 2.6–2.9 (m. 4H); 2.8–3.3 (complex multiplet, 1H); 6.5 (s, 1H).

EXAMPLE 6

2-methyl-5,6-dihydro-4H-cyclopenta[b]thiophene-6-ethylcarboxylate: ($C_{11}H_{14}O_2S$)

A solution of 19.3 g of 2-methyl-5,6-dihydro-4H-cyclopenta[b]thiophene-6-carboxylic acid and 10 cc of sulfuric acid in 500 cc of ethanol was refluxed for 8 hours then concentrated under reduced pressure to a volume of 100 cc. The residue was diluted with ethyl acetate and stirred with an aqueous solution of sodium bicarbonate. The organic phase was separated, washed with water and dried over sodium sulfate. After evaporation of the solvent under reduced pressure the residue was distilled. 18.2 g (yield=81%) of ethyl-2-methyl-5,6-dihydro-4H-cyclopenta[b]thiophene-6-carboxylate was obtained. Bp0.7=90° C.

| Analysis in percent | C % | H % | S % |
|---|---|---|---|
| Calculated | 62.82 | 6.71 | 15.25 |
| Found | 63.15 | 6.73 | 14.95 |

IR $\nu(C=O) = 1740$ cm$^{-1}$.

NMR (CDCl$_3$) $\delta = 1.3$ (t, 3H); 2.5 (s, 3H); 2.6–3.0 (complex multiplet, 4H); 3.5–4.5 (complex multiplet, 3H); 6.5 (s, 1H).

EXAMPLE 7

3-Benzoyl-2-methyl-5,6-dihydro-4H-cyclopenta[b]thiophene-6-carboxylic acid (a)
3-benzoyl-2-methyl-5,6-dihydro-4H-cyclopenta[b]thiophene-6-ethylcarboxylate: ($C_{18}H_{18}O_3S$)

85 g (0.64 mole) of aluminum chloride was added to a solution, kept at 20° C., of 47.5 g (0.226 mole) of 2-methyl-5,6-dihydro-4H-cyclopenta[b]thiophene-6-ethylcarboxylate and 42 g (0.30 mole) of benzoyl chloride in 500 cc of methylene chloride. The mixture was refluxed for 7 hours. After cooling at ambient temperature, the reaction mixture was poured into an ice-hydrochloric acid mixture. The organic phase was separated. The aqueous phase was extracted with methylene chloride. The organic solutions were collected, washed with water and dried on sodium sulfate. The solvent was evaporated and the residue distilled. 59.7 g (yield=84%) of 3-benzoyl-2-methyl-5,6-dihydro-4H-cyclopenta[b]thiophene-6-ethylcarboxylate was obtained. Bp1=178°–183° C.

| Analysis in percent | C % | H % | S % |
|---|---|---|---|
| Calculated | 68.76 | 5.77 | 10.20 |

| Analysis in percent | C % | H % | S % |
| --- | --- | --- | --- |
| Found | 68.74 | 5.77 | 10.03 |

IR $\nu(C=O)=1735$ and $1650$ cm$^{-1}$.

NMR (CDCl$_3$) $\delta=1.3$ (t, 3H); 2.3–2.9 (m, 7H); 3.5–4.5 (m, 3H); 7.2–8.0 (complex multiplet, 5H).

(b)

3-Benzoyl-2-methyl-5,6-dihydro-4H-cyclopenta[b]thiophene-6-carboxylic acid : (C$_{16}$H$_{14}$O$_3$S)

A solution of 9.5 g (0.031 mole) of 3-benzoyl-2-methyl-5,6-dihydro-4H-cyclopenta[b]thiophene-6-ethylcarboxylate in 250 cc of ethanol was added to a solution of 6.6 g (0.062) of sodium carbonate in 150 cc of water. The mixture was refluxed for 2 hours then evaporated dry under reduced pressure. The residue was picked up with water. The solution was washed with ethyl acetate then acidified with dilute hydrochloric acid. The 3-benzoyl-2-methyl-5,6-dihydro-4H-cyclopenta[b]thiophene-6-carboxylic acid separated. It was filtered, washed with water, dried and recrystallized in a hexane-ethyl acetate mixture. Mp=145°–147° C. Yield=5 g (59%).

| Analysis in percent | C % | H % | S % |
| --- | --- | --- | --- |
| Calculated | 67.11 | 4.93 | 11.20 |
| Found | 67.25 | 4.93 | 11.19 |

NMR (CDCl$_3$) $\delta=2.4$–3.0 (m, 7H); 3.9–4.4 (complex multiplet, 1H); 7.3–8.0 (complex multiplet, 5H); 10.9–11.4 (broadened peak, 1H, exchangeable with CF$_3$COOD).

EXAMPLE 8

2-methyl-5,6-dihydro-4H-cyclopenta[b]thiophene-6-methylcarboxylate: (C$_{10}$H$_{12}$O$_2$S)

A solution of 9.4 g (0.051 mole) of 2-methyl-5,6-dihydro-4H-cyclopenta[b]thiophene-6-carboxylic acid and 0.4 g of paratoluenesulfonic acid monohydrate in 400 cc of methanol was stirred at ambient temperature for 20 hours then concentrated dry under reduced pressure. The residue was picked up with ethyl acetate. The resulting solution was washed with an aqueous solution of sodium bicarbonate then water. It was dried on sodium sulfate. After evaporation of the solvent under reduced pressure, the residue was distilled. 7.5 g (yield=74%) of methyl 2-methyl-5,6-dihydro-4H-cyclopenta[b]thiophene-6-carboxylate was obtained. Bp0.6=107° C.

| Analysis in percent | C % | H % | S % |
| --- | --- | --- | --- |
| Calculated | 61.19 | 6.17 | 16.34 |
| Found | 61.06 | 5.96 | 16.24 |

IR $\nu(C=O)=1740$ cm$^{-1}$.

NMR (CCl$_4$) $\delta=1.4$ (s, 3H); 2.5–2.9 (m, 4H); 3.6 (s, 3H); 3.5–4.2 (m, 1H); 6.3 (s, 1H).

EXAMPLE 9

3-Benzoyl-2-methyl-5,6-dihydro-4H-cyclopenta[b]thiophene-6-carboxylic acid (a)

3-benzoyl-2-methyl-5,6-dihydro-4H-cyclopenta[b]thiophene-6-methylcarboxylate: (C$_{17}$H$_{16}$O$_3$S)

To a suspension of 43.1 g (0.32 mole) of aluminum chloride in 260 cc of methylene chloride kept at 5° C. were successively added a solution of 16 g (0.081 mole) of 2-methyl-5,6-dihydro-4H-cyclopenta[b]thiophene-6-methylcarboxylate in 10 cc of methylene chloride then 21.3 g (0.15 mole) of benzoyl chloride. The mixture was refluxed for 4 hours. After cooling to ambient temperature, the reaction medium was poured into an ice-hydrochloric acid mixture. The organic phase was separated. The aqueous phase was extracted with methylene chloride. The organic solutions were collected, washed with water and dried on sodium sulfate. Evaporation of the solvent under reduced pressure provided a residue that was solidified in a little hexane. 22.2 g (yield=90%) of 3-benzoyl-2-methyl-5,6, dihydro-4H-cyclopenta[b]thiophene-6-methylcarboxylate melting at 70°–74° C. was obtained.

An analytical sample was obtained by recrystallization in a hexane-ethylacetate mixture. Mp=78°–80° C.

| Analysis in percent | C % | H % | S % |
| --- | --- | --- | --- |
| Calculated | 67.97 | 5.37 | 10.68 |
| Found | 67.83 | 5.36 | 10.89 |

IR $\nu(C=O)=1740$ and $1660$ cm$^{-1}$.

(b)

3-Benzoyl-2-methyl-5,6-dihydro-4H-cyclopenta[b]thiophene-6-carboxylic acid: (C$_{16}$H$_{14}$O$_3$ S)

A solution of 22 g (0.073 mole) of 3-benzoyl 2-methyl 5,6-dihydro-4H-cyclopenta[b]thiophene-6-methylcarboxylate in 130 cc of ethanol was added to a solution of 15.6 g (0.148 mole) of sodium carbonate in 270 cc of water. The mixture was refluxed for 2 hours then evaporated dry under reduced pressure. The residue was picked up with water. The solution was washed with ether then acidified with dilute hydrochloric acid. The solid that separated was filtered, washed with water, dried and recrystallized in toluene. 7 g (yield=80%) of 3-benzoyl-2-methyl-5,6-dihydro-4H-cyclopenta[b]thiophene-6-carboxylic acid (mp=145°–147° C.) was obtained that was identical in all respects with that obtained in example 7.

EXAMPLE 10

2-Methyl 3-(2-thenoyl)-5,6-dihydro-4H-cyclopenta[b]thiophene-6-carboxylic acid: (C$_{14}$H$_{12}$O$_3$S$_2$)

By operating as in example 7 starting with 10 g (0.048 mole) of 2-methyl 5,6-dihydro-4H-cyclopenta[b]thiophene-6-ethylcarboxylate, 16 g (0.12 mole) of aluminum chloride and 12.6 g (0.085 mole) of 2-thenoyl chloride, there was obtained 9.5 g (yield=62%) of 2-methyl-3-(2-thenoyl)5,6-dihydro-4H-cyclopenta[b]thiophene-6-ethylcarboxylate. Saponification of 9.5 g of this ester under the conditions of example 7 provided 5.8 g (yield=66%) of the desired acid. Mp=128°–130° C. (hexane-ethyl acetate).

| Analysis in percent | C % | H % | S % |
|---|---|---|---|
| Calculated | 57.51 | 4.14 | 21.93 |
| Found | 57.22 | 4.02 | 21.80 |

EXAMPLE 11

3-(4-chlorobenzoyl)-2-methyl-5,6-dihydro-4H-cyclopenta[b]thiophene-6-carboxylic acid: ($C_{16}H_{13}ClO_3S$)

By operating as in example 7 starting from 7 g (0.033 mole) of 2-methyl-5,6-dihydro-4H-cyclopenta[b]thiophene-6-ethylcarboxylate, 10.8 g (0.062 mole) of 4-chlorobenzoyl chloride and 17.7 g (0.133 mole) of aluminum chloride, there was obtained 9.9 g (yield=85%) of 3-(4-chlorobenzoyl)-2-methyl-5,6-dihydro-4H-cyclopenta[b]thiophene-6-ethylcarboxylate.
Bp1=198°-202° C. Saponification of this ester under the conditions of example 7 provided 5.8 g (yield=64%) of the desired acid. Mp=139°-141° C. (hexane-ethyl acetate).

| Analysis in percent | C % | H % | Cl % | S % |
|---|---|---|---|---|
| Calculated | 59.90 | 4.08 | 11.05 | 10.00 |
| Found | 60.12 | 3.95 | 11.09 | 9.88 |

EXAMPLE 12

3-(2-chlorobenzoyl)-2-methyl-5,6-dihydro-4H-cyclopenta[b]thiophene-6-carboxylic acid: ($C_{16}H_{13}ClO_3S$)

By operating as in example 7 starting from 7 g (0.033 mole) of 2-methyl-5,6-dihydro-4H-cyclopenta[b]thiophene-6-ethylcarboxylate, 10.8 g (0.062 mole) of 2-chlorobenzoyl chloride and 17.7 g (0.133 mole of aluminum chloride, there was obtained 8.6 g (yield=74%) of 3-(2-chlorobenzoyl)-2-methyl-5,6-dihydro-4H-cyclopenta[b]thiophene-6-ethylcarboxylate.
Bp1=193°-197° C. Saponification of this ester under the conditions of example 7 provided 2.5 g (yield=32%) of the desired acid. Mp=113°-115° C. (hexane-ethyl acetate).

| Analysis in percent | C % | H % | Cl % | S % |
|---|---|---|---|---|
| Calculated | 59.90 | 4.08 | 11.05 | 10.00 |
| Found | 60.02 | 4.17 | 11.16 | 9.85 |

EXAMPLE 13

2-Methyl-3-(4-methylbenzoyl)-5,6-dihydro-4H-cyclopenta[b]thiophene-6-carboxylic acid: ($C_{17}H_{16}O_3S$)

By operating as in example 7 starting from 7 g (0.033 mole) of 2-methyl-5,6-dihydro-4H-cyclopenta[b]thiophene-6-ethylcarboxylate, 9.5 g (0.062 mole) of 4-methylbenzoyl chloride and 17.7 g (0.133 mole) of aluminum chloride, there was obtained 10.3 g (yield=97%) of 2-methyl-3-(4-methylbenzoyl)-5,6-dihydro-4H-cyclopenta[b]thiophene-6-ethylcarboxylate.
Bp1=194°-198° C. Saponification of this ester under the conditions of example 7 provided 6.1 g (yield=65%) of the desired acid. Mp=150°-152° C. (hexane-ethyl acetate).

| Analysis in percent | C % | H % | S % |
|---|---|---|---|
| Calculated | 67.97 | 5.37 | 10.68 |
| Found | 67.81 | 5.29 | 10.69 |

EXAMPLE 14

3-(2-furoyl)-2-methyl-5,6-dihydro-4H-cyclopenta[b]thiophene-6-carboxylic acid: ($C_{14}H_{12}O_4S$)

By operating as in example 7 starting from 5.5 g (0.026 mole) of 2-methyl-5,6-dihydro-4H-cyclopenta[b]thiophene-6-ethylcarboxylate, 6.6 g (0.051 mole) of 2-furoyl chloride and 14.4 g (0.108 mole) of aluminum chloride, there was obtained 2.5 g (yield=32%) of ethyl-3-(2-furoyl)-2-methyl-5,6-dihydro-4H-cyclopenta[b]-thiophene-6-carboxylate. Saponification of this ester under the conditions of example 7 provided 1.2 g (yield=53%) of the desired acid. Mp=120°-122° C. (hexane-ethyl acetate).

| Analysis in percent | C % | H % | S % |
|---|---|---|---|
| Calculated | 60.85 | 4.38 | 11.60 |
| Found | 60.75 | 4.35 | 11.59 |

EXAMPLE 15

2-Methyl-3-(3-methylbenzoyl)-5,6-dihydro-4H-cyclopenta[b]thiophene-6-carboxylic acid: ($C_{17}H_{16}O_3S$)

By operating as in example 7 starting from 9.1 g (0.043 mole) of 2-methyl-5,6-dihydro-4H-cyclopenta[b]thiophene-6-ethylcarboxylate, 12.4 g (0.081 mole) of 3-methylbenzoyl chloride and 23 g (0.173 mole) of aluminum chloride, there was obtained 12 g (yield=84%) of 2-methyl-3-(3-methylbenzoyl)-5,6-dihydro-4H-cyclopenta[b]thiophene-6-ethylcarboxylate. Bp1=190°-195° C. Saponification of this ester under the conditions of example 7 provided 7.8 g (yield=71%) of the desired acid. Mp=98°-100° C. (hexane-ethyl acetate).

| Analysis in percent | C % | H % | S % |
|---|---|---|---|
| Calculated | 67.97 | 5.37 | 10.67 |
| Found | 67.70 | 5.43 | 10.61 |

EXAMPLE 16

3-(4-Methoxybenzoyl)-2-methyl-5,6-dihydro-4H-cyclopenta[b]thiophene-6-carboxylic acid: ($C_{17}H_{16}O_4S$)

By operating as in example 7 starting from 9.1 g (0.043 mole) of 2-methyl-5,6-dihydro-4H-cyclopenta[b]thiophene-6-ethylcarboxylate, 13.7 g (0.081 mole) of 4-methoxybenzoyl chloride and 23 g (0.173 mole) of aluminum chloride, there was obtained 11 g (yield=74%) of 3-(4-methoxybenzoyl)-2-methyl-5,6-dihydro-4H-cyclopenta[b]thiophene-6-ethylcarboxylate. Bp1=203°-207° C. Saponification of this ester under the conditions of example 7 provided 7 g (yield=69%) of the desired acid. Mp=120°-122° C. (hexane-ethyl acetate).

| Analysis in percent | C % | H % | S % |
|---|---|---|---|
| Calculated | 64.54 | 5.10 | 10.14 |

| Analysis in percent | C % | H % | S % |
|---|---|---|---|
| Found | 64.36 | 5.17 | 10.27 |

EXAMPLE 17

3-(3-Chlorobenzoyl)-2-methyl-5,6-dihydro-4H-cyclopenta[b]thiophene-6-carboxylic acid: ($C_{16}H_{13}ClO_3S$)

By operating as in example 7 starting from 9.1 g (0.043 mole) of 2-methyl-5,6-dihydro-4H-cyclopenta[b]thiophene-6-ethylcarboxylate, 14 g (0.081 mole) of 3-chlorobenzoyl chloride and 23 g (0.173 mole) of aluminum chloride, there was obtained 12.1 g (yield=80%) of 3-(3-chlorobenzoyl)-2-methyl-5,6-dihydro-4H-cyclopenta[b]thiophene-6-ethylcarboxylate. Bp1=205°–209° C. Saponification of this ester under the conditions of example 7 provided 6.2 g (yield=57%) of the desired acid. Mp=100°–102° C. (hexane-ethyl acetate).

| Analysis in percent | C % | H % | Cl % | S % |
|---|---|---|---|---|
| Calculated | 59.90 | 4.08 | 11.05 | 9.99 |
| Found | 60.09 | 4.16 | 10.99 | 9.94 |

EXAMPLE 18

2-Methyl-3-(2-methylbenzoyl)-5,6-dihydro4H-cyclopenta[b]thiophene-6-carboxylic acid: ($C_{17}H_{16}O_3S$)

By operating as in example 7, starting from 9.1 g (0043 mole) of 2-methyl-5,6-dihydro-4H-cyclopenta[b]-thiophene-6-ethylcarboxylate, 12.4 g (0.081 mole) of 2-methylbenzoyl chloride and 23 g (0.173 mole) of aluminum chloride, there was obtained 11.2 g (yield=79%) of 2-methyl-3-(2-methylbenzoyl)-5,6-dihydro-4H-cyclopenta[b]thiophene-6-ethylcarboxylate. Bp1=200°–205° C. Saponification of this ester under the conditions of example 7 provided 6 g (yield=58%) of the desired acid. Mp=110°–112° C. (hexane-ethyl acetate).

| Analysis in percent | C % | H % | S % |
|---|---|---|---|
| Calculated | 67.97 | 5.37 | 10.68 |
| Found | 67.88 | 5.44 | 10.51 |

EXAMPLE 19

2-Methyl-3-(5-methyl-2-thenoyl)-5,6-dihydro-4H-cyclopenta[b]thiophene-6-carboxylic acid: ($C_{15}H_{14}O_3S_2$)

By operating as in example 9, starting from 7 g (0.032 mole) of 2-methyl-5,6-dihydro-4H-cyclopenta[b]thiophene-6-ethylcarboxylate, 10 g (0.062 mole) of 5-methyl-2-thenoyl chloride and 17.7 g (0.133 mole) of aluminum chloride, there was obtained 9.1 g (yield=84% of 2-methyl-3-(5-methyl-2-thenoyl) 5,6-dihydro-4H-cyclopenta[b]thiophene-6-ethylcarboxylate. Bp0.6=180° C. Saponification of this ester under the conditions of example 9 provided 6 g (yield=72%) of the desired acid. Mp=158°–160° C. (hexane-ethyl acetate).

| Analysis in percent | C % | H % | S % |
|---|---|---|---|
| Calculated | 58.80 | 4.61 | 20.93 |
| Found | 58.90 | 4.68 | 21.20 |

EXAMPLE 20

3-(5-Chloro-2-thenoyl)-2-methyl-5,6-dihydro-4H-cyclopenta[b]thiophene-6-carboxylic acid: ($C_{14}H_{11}ClO_3S_2$)

By operating as in example 9 starting from 8.3 g (0.042 mole) of 2-methyl-5,6-dihydro-4H-cyclopenta[b]thiophene-6-methylcarboxylate, 12 g (0.08 mole) of 5-chloro-2-thenoyl chloride and 23.2 g (0.174 mole) of aluminum chloride, there was obtained 11.5 g (yield=80%) of 3-(5-chloro-2-thenoyl)-2-methyl-5,6-dihydro-4H-cyclopenta[b]thiophene-6-methylcarboxylate. Saponification of this ester under the conditions of example 9 provided, after filtration on a silica column (3/2 hexane-acetone eluant) and recrystallization in a hexane-ethyl acetate mixture, 7.7 g (yield=70%) of the desired acid. Mp=128°–130° C.

| Analysis in percent | C % | H % | Cl % | S % |
|---|---|---|---|---|
| Calculated | 51.45 | 3.39 | 10.85 | 19.62 |
| Found | 51.38 | 3.21 | 11.01 | 19.66 |

EXAMPLE 21

3-(4-Fluorobenzoyl)-2-methyl-5,6-dihydro-4H-cyclopenta[b]thiophene-6-carboxylic acid: ($C_{16}H_{13}FO_3S$)

By operating as in example 9 starting from 7 g (0.032 mole) of 2-methyl-5,6-dihydro-4H-cyclopenta[b]thiophene-6-ethylcarboxylate, 9.8 g (0.062 mole) of 4-fluorobenzoyl chloride and 17.7 g (0.133 mole) of aluminum chloride, there was obtained 10.3 g (yield=95%) of 3-(4-fluorobenzoyl)-2-methyl-5,6-dihydro-4H-cyclopenta[b]thiophene-6-ethylcarboxylate.
Bp0.6=185° C. Saponification of this ester under the conditions of example 9 provided 6.5 g (yield=69%) of the desired acid. Mp=100°–102° C. (hexane-ethyl acetate).

| Analysis in percent | C % | H % | F % | S % |
|---|---|---|---|---|
| Calculated | 63.14 | 4.30 | 6.24 | 10.54 |
| Found | 63.28 | 4.31 | 6.22 | 10.29 |

EXAMPLE 22

3-(3-Methoxybenzoyl)-2-methyl-5,6-dihydro-4H-cyclopenta[b]thiophene-6-carboxylic acid: ($C_{17}H_{16}O_4S$)

By operating as in example 9 starting from 7 g (0.032 mole) of 2-methyl-5,6-dihydro-4H-cyclopenta[b]thiophene-6-ethylcarboxylate, 10.5 g (0.061 mole) of 3-methoxybenzoyl chloride and 17.7 g (0.133 mole) of aluminum chloride, there was obtained 10.2 g (yield=92%) of 3-(3-methoxy-benzoyl)-2-methyl-5,6-dihydro-4H-cyclopenta[b]thiophene-6-ethylcarboxylate. Bp0.6=195° C. Saponification of this ester under the conditions of example 9 provided 7.3 g (yield=79%) of the desired acid. Mp=121°–123° C. (hexane-ethyl acetate).

| Analysis in percent | C % | H % | S % |
|---|---|---|---|
| Calculated | 64.54 | 5.10 | 10.14 |
| Found | 64.59 | 5.06 | 9.97 |

EXAMPLE 23

3-(3,4-dichlorobenzoyl)-2-methyl-5,6-dihydro-4H-cyclopenta[b]thiophene-6-carboxylic acid: ($C_{16}H_{12}Cl_2O_3S$)

By operating as in example 9 starting from 8.5 g (0.04 mole) of 2-methyl-5,6-dihydro-4H-cyclopenta[b]thiophene-6-ethylcarboxylate, 15.9 g (0.076 mole) of 3,4-dichlorobenzoyl chloride and 21.6 g (0.162 mole) of aluminum chloride, there was obtained 8.8 g (yield=57%) of 3-(3,4-dichloro-benzoyl)-2-methyl-5,6-dihydro-4H-cyclopenta[b]thiophene-6-ethylcarboxylate. Bp0.6=206° C. Saponification of this ester under the conditions of example 9 provided 3.5 g (yield=44%) of the desired acid. Mp=119°-121° C. (hexane-ethylacetate).

| Analysis in percent | C % | H % | Cl % | S % |
|---|---|---|---|---|
| Calculated | 54.09 | 3.41 | 19.96 | 9.03 |
| Found | 54.00 | 3.51 | 19.80 | 9.14 |

EXAMPLE 24

2-Methyl-3-(4-nitrobenzoyl)-5,6-dihydro-4H-cyclopenta[b]thiophene-6-carboxylic acid (a)

2-methyl-3-(4-nitrobenzoyl)-5,6-dihydro-4H-cyclopenta[b]thiophene-6-methylcarboxylate: ($C_{17}H_{15}NO_5S$)

By operating as in example 9 starting from 11.4 g (0.058 mole) of 2-methyl-5,6-dihydro-4H-cyclopenta[b]thiophene-6-methylcarboxylate, 20.6 g (0.111 mole) of 4-nitrobenzoyl chloride and 31.9 g (0.24 mole) of aluminum chloride, there was obtained, after filtration on silica (4/1 hexane-ethyl acetate eluant) 15.6 g (yield=78%) of 2-methyl-3-(4-nitrobenzoyl)-5,6-dihydro-4H-cyclopenta[b]thiophene-6-methylcarboxylate (Mp=98°-100° C.) used in the next stage without further purification.

An analytical sample was obtained by recrystallization in a hexane-ethyl acetate mixture. Mp=105°-108° C.

| Analysis in percent | C % | H % | N % | S % |
|---|---|---|---|---|
| Calculated | 59.12 | 4.38 | 4.06 | 9.28 |
| Found | 59.05 | 4.46 | 4.14 | 9.47 |

(b)

2-Methyl-3-(4-nitrobenzoyl)-5,6-dihydro-4H-cyclopenta[b]thiophene-6-carboxylic acid: ($C_{16}H_{13}NO_5S$)

A mixture of 3.9 g (0.011 mole) of 2-methyl-3-(4-nitrobenzoyl)-5,6-dihydro-4H-cyclopenta[b]thiophene-6-methylcarboxylate and 260 cc of 10N hydrochloric acid was refluxed for 3 hours. After cooling to ambient temperature, the reaction medium was poured into an ice-hydrochloric acid mixture and extracted with ether. The ether phase was washed with water, dried on sodium sulfate and concentrated under reduced pressure. The residue was filtered on a silica column (3/2 hexane-acetone eluant) then recrystallized in a hexane-ethyl acetate mixture. 3.4 g (yield 63%) of 2-methyl-3-(4-nitro-benzoyl)-5,6-dihydro-4H-cyclopenta[b]thiophene-6-carboxylic acid was obtained. Mp=156°-158° C.

| Analysis in percent | C % | H % | N % | S % |
|---|---|---|---|---|
| Calculated | 58.00 | 3.95 | 4.23 | 9.68 |
| Found | 57.80 | 3.68 | 4.13 | 9.73 |

EXAMPLE 25

3-(2-Hydroxybenzoyl)-2-methyl-5,6-dihydro-4H-cyclopenta[b]thiophene-6-carboxylic acid: ($C_{16}H_{14}O_4S$)

By operating as in example 9 starting from 10 g (0.051 mole) of 2-methyl-5,6-dihydro-4H-cyclopenta[b]thiophene-6-methylcarboxylate, 16.6 g (0.097 mole) of 2-methoxybenzoyl chloride and 28 g (0.21 mole) of aluminum chloride, there was obtained 13.8 g of 3-(2-hydroxybenzoyl)-2-methyl-5,6-dihydro-4H-cyclopenta[b]thiophene-6-methylcarboxylate. Saponification of this raw ester under the conditions of example 9 provided the desired acid, purified by filtration on a silica column (3/2 hexane-acetone eluant) then by recrystallization in a hexane-ethyl acetate mixture. Yield=4.1 g (31%). Mp=117°-120° C.

| Analysis in percent | C % | H % | N % |
|---|---|---|---|
| Calculated | 63.56 | 4.67 | 10.61 |
| Found | 63.47 | 4.51 | 10.88 |

EXAMPLE 26

3-(2-Methoxybenzoyl)-2-methyl-5,6-dihydro-4H-cyclopenta[b]thiophene-6-carboxylic acid: ($C_{17}H_{16}O_4S$)

A mixture of 10.4 g (0.034 mole) of 3-(2-hydroxybenzoyl)-2-methyl-5,6-dihydro-4H-cyclopenta[b]thiophene-6-methylcarboxylate, 21 g (0.152 mole) of potassium carbonate and 100 cc of methyl ethyl ketone was refluxed for 5 minutes then cooled to ambient temperature. 13.3 g (0.094 mole) of methyl iodide was added and reflux for 1 hour was again performed. The reaction medium was filtered. The filtrate was concentrated under reduced pressure. The residue was dissolved in ethyl acetate and the solution washed with 1N sodium hydroxide solution then dried on sodium sulfate. Evaporation of the solvent provided 10.6 g of 3-(2-methoxybenzoyl)-2-methyl-5,6-dihydro-4H-cyclopenta[b]thiophene-6-methylcarboxylate which was dissolved in 60 cc of ethanol. This solution was added to a solution of 7.4 g (0.07 mole) of sodium carbonate in 120 cc of water. The mixture was refluxed for 2 hours then evaporated dry under reduced pressure. The residue was picked up with water. The solution was washed with ether then acidified by dilute hydrochloric acid. The solid which separated was purified by filtration on silica (3/2 hexane-acetone eluant) then recrystallized in a hexane-ethyl acetate mixture. Yield=7.5 g (76%). Mp=126°-128° C.

| Analysis in percent | C % | H % | S % |
|---|---|---|---|
| Calculated | 64.54 | 5.10 | 10.14 |
| Found | 64.18 | 5.14 | 10.17 |

EXAMPLE 27

3-(4-Dimethylaminobenzoyl)-2-methyl-5,6-dihydro-4H-cyclopenta[b]thiophene-6-carboxylic acid (a) 3-(4-dimethylaminobenzoyl)-2-methyl-5,6-dihydro-4H-cyclopenta[b]thiophene-6-methylcarboxylate ($C_{19}H_{21}NO_3S$)

A mixture of 4.2 g (0.012 mole) of 2-methyl-3-(4-nitrobenzoyl)-5,6-dihydro-4H-cyclopenta[b]thiophene-6-methylcarboxylate, 60 cc of methanol, 5 cc of a 40% aqueous formaldehyde solution, 0.4 cc of propionic acid and 0.6 g of Raney nickel was hydrogenated at 50° C. under 100 atm for 6 hours. The catalyst was removed by filtration. The filtrate was concentrated dry under reduced pressure. The residue was dissolved in ethyl acetate and the resulting solution was washed with an aqueous sodium bicarbonate solution then with water. It was dried on sodium sulfate. After evaporation of the solvent under reduced pressure, there was obtained 4 g (yield=97%) of 3-(4-dimethylaminobenzoyl)-2-methyl-5,6-dihydro-4H-cyclopenta[b]thiophene-6-methylcarboxylate used in the next stage without further purification.

IR$\nu$(C=O)=1730 cm$^{-1}$.

NMR (CDCl$_3$) $\delta$=2.4 (s, 3H); 2.5–2.8 (m, 4H); 3.0 (s, 6H); 3.6–3.8 (m, 4H); 6.6 (d, 2H); 7.7 (d, 2H).

(b) 3-(4-Dimethylaminobenzoyl)-2-methyl-5,6-dihydro-4H-cyclopenta[b]thiophene-6-carboxylic acid: ($C_{18}H_{19}NO_3S$)

A solution of 4 g (0.012 mole) of the ester obtained above in 30 cc of ethanol was added to a solution of 2.4 g (0.023 mole) of sodium carbonate in 40 cc of water. The mixture was refluxed for 2 hours then evaporated dry under reduced pressure. The residue was dissolved in water. The solution was washed in ether then acidified to pH 5 by dilute acetic acid. The mixture was extracted by ethyl acetate. The organic phase was separated, dried on sodium sulfate and concentrated under reduced pressure. Recrystallization of the residue in a hexane-ethyl acetate mixture provided 1.8 g (yield=46%) of the desired acid. Mp=171°–173° C.

| Analysis in percent | C % | H % | N % | S % |
| --- | --- | --- | --- | --- |
| Calculated | 65.63 | 5.81 | 4.25 | 9.73 |
| Found | 65.47 | 5.83 | 4.01 | 9.69 |

EXAMPLE 28

(5-isobutyl-2-thienyl)succinic acid (a) Diethyl(5-isobutyl-2-thienyl)methylene malonate: ($C_{16}H_{22}O_4S$)

295 g (1.84 mole) of ethyl malonate was added to a mixture of 242 g (1.44 mole) of 5-isobutyl-2-thiophenecarboxaldehyde (obtained according to the process described by N. P. Buu-Hoi et al., J. Chem. Soc. 1951, 4590), 45 cc of acetic acid, 45 cc of piperidine and 1550 cc of benzene. The reaction mixture was refluxed for 2 hours while the resulting water was eliminated by a Dean-Stark apparatus then it was concentrated under reduced pressure. The residue was picked up with methylene chloride. The organic phase was washed with water, dried on sodium sulfate and concentrated. Distillation of the residue provided 417.2 g (yield=93%) of diethyl (5-isobutyl-2-thienyl)methylene malonate. Bp1=163°–167° C.

| Analysis in percent | C % | H % | S % |
| --- | --- | --- | --- |
| Calculated | 61.91 | 7.15 | 10.33 |
| Found | 62.18 | 7.01 | 10.26 |

IR$\nu$(C=O)=1730 cm$^{-1}$.

NMR (CDCl$_3$) $\delta$=1.0 (d, 6H); 1.2–2.3 (m, 7H); 2.7 (d, 2H); 4.1–4.7 (m, 4H); 6.8 (d, 1H); 7.3 (d, 1H); 7.8 (s, 1H).

(b) (5-isobutyl-2-thienyl)Succinic acid: ($C_{12}H_{16}O_4S$)

A solution of 169 g (2.60 mole) of potassium cyanide in 580 cc of water was added to a solution of 415 g (1.33 mole) of diethyl (5-isobutyl-2-thienyl) methylene malonate in 2300 cc of ethanol. The mixture was refluxed for 3 hours. Then a solution of 63 g (1.57 mole) of sodium hydroxide in 580 cc of water was added and refluxed for 1 hour. The ethanol was eliminated by distillation, while the volume of the reaction mixture was kept constant by simultaneous addition of water. After cooling to ambient temperature, hydrochloric acid was added to pH 1 and reflux was again performed for 45 minutes. The mixture was extracted with ethyl acetate. The organic solution itself was extracted by an aqueous potassium carbonate solution. The aqueous phase was separated and acidified with dilute hydrochloric acid. The precipitate was filtered, washed with water and dried. It was purified by recrystallization in a hexane-ethyl acetate mixture; 250.2 g (yield=73%) of (5-isobutyl-2-thienyl)succinic acid was obtained. Mp=106°–108° C.

| Analysis in percent | C % | H % | S % |
| --- | --- | --- | --- |
| Calculated | 56.23 | 6.29 | 12.51 |
| Found | 56.18 | 6.57 | 12.50 |

IR$\nu$(C=O)=1700 cm$^{-1}$ (wide).

NMR (CDCl$_3$) $\delta$=1.0 (d, 6H); 1.5–2.2 (m, 1H); 2.7 (d, 2H); 2.9–3.6 (m, 2H); 4.1–4.6 (m, 1H); 6.7 (d, 1H); 6.9 (d, 1H).

EXAMPLE 29

2-Isobutyl-4-oxo-5,6-dihydro-4H-cyclopenta[b]thiophene-6-carboxylic acid (a) (5-isobutyl-2-thienyl)succinic anhydride: ($C_{12}H_{14}O_3S$)

10 g of (5-isobutyl-2-thienyl)succinic acid was added to 40 cc of acetyl chloride and the mixture was refluxed for 1 hour 30 minutes. The excess acetyl chloride was evaporated under reduced pressure. Distillation of the residue provided 7.9 g (yield=85%) of (5-isobutyl-2-thienyl)succinic anhydride.

Bp0.4=155° C.

| Analysis in percent | C % | H % | S % |
| --- | --- | --- | --- |
| Calculated | 60.48 | 5.92 | 13.46 |
| Found | 60.28 | 6.04 | 13.25 |

IR$\nu$(C=O)=1870 and 1790 cm$^{-1}$.

(b)
2-Isobutyl-4-oxo-5,6-dihydro-4H-cyclopenta[b]thiophene-6-carboxylic acid: ($C_{12}H_{14}O_3S$)

A solution of 5.2 g (0.022 mole) of (5-isobutyl-2-thienyl)succinic anhydride in 20 cc of nitrobenzene was added drop by drop to a solution of 8 g (0.06 mole) of aluminum chloride in 40 cc of nitrobenzene. The mixture was brought to 40C for 1 hour. After cooling to ambient temperature, the reaction mixture was poured into an ice-hydrochloric acid mixture, then extracted with methylene chloride. The organic solution was extracted with an aqueous sodium carbonate solution. The aqueous phase was acidified by dilute hydrochloric acid. The oil that separated was extracted with ethyl acetate. After elimination of the solvent under reduced pressure, the residue was purified by chromatography on a silica column (9/1/0.05 methylene chloride-methanol-acetic acid eluant). 2.3 g (yield=44%) of 2-isobutyl-4-oxo-5,6-dihydro-4H-cyclopenta[b]thiophene-6-carboxylic acid melting at 80° C. was obtained and used in the next stage without further purification. An analytical sample was obtained by recrystallization in a hexane-ethyl acetate mixture.
Mp=88°–90° C.

| Analysis in percent | C % | H % | S % |
|---|---|---|---|
| Calculated | 60.48 | 5.92 | 13.45 |
| Found | 60.18 | 5.85 | 13.31 |

IR$\nu$(C=O)=1745 and 1660 cm$^{-1}$.
NMR (CDCl$_3$) $\delta$=1.0 (d, 6H); 1.7–2.3 (m, 1H); 2.8 (d, 2H); 3.2–3.5 (m, 2H); 4.3–4.6 (m, 1H); 6.9 (s, 1H); 10.5 (s, 1H), exchangeable by CF3COOD).

EXAMPLE 30
2-Isobutyl-5,6-dihydro-4H-cyclopenta[b]thiophene-6-carboxylic acid: ($C_{12}H_{16}O_2S$)

Obtained by operating as in example 5 by reduction of 20 g (0.084 mole) of 2-isobutyl-4-oxo-5,6-dihydro-4H-cyclopenta[b]thiophene-6-carboxylic acid by a zinc amalgam prepared from 56.1 g (0.86 g at) of zinc powder and 5.6 g (0.021 mole) of mercuric chloride. Yield=14.2 g (75%). An analytical sample was obtained by recrystallization in heptane. Mp=50°–51° C.

| Analysis in percent | C % | H % | S % |
|---|---|---|---|
| Calculated | 64.25 | 7.19 | 14.30 |
| Found | 64.46 | 7.21 | 14.16 |

IR$\nu$(C=O)=1690 cm$^{-1}$.
NMR (CDCl$_3$) $\delta$=0.9 (d, 6H), 1.4–2.3 (m, 1H); 2.4–3.0 (complex multiplet, 6H); 3.8–4.3 (complex multiplet, 1H); 10.3–10.8 (broadened peak, 1H exchangeable by CF3COOD).

EXAMPLE 31
Ethyl-2-isobutyl-5,6-dihydro-4H-cyclopenta[b]thiophene-6-carboxylate: ($C_{14}H_{20}O_2S$)

Obtained by operating as in example 6 starting from 14.2 g (0.063 mole) of 2-isobutyl-5,6-dihydro-4H-cyclopenta[b]thiophene-6-carboxylic acid, 6 cc of sulfuric acid and 300 cc of ethanol. Yield=10.5 g (66%). Bp0.6=103°–107° C.

| Analysis in percent | C % | H % | S % |
|---|---|---|---|
| Calculated | 66.63 | 7.99 | 12.71 |
| Found | 66.81 | 8.19 | 12.68 |

IR$\nu$(C=O)=1735 cm$^{-1}$.

EXAMPLE 32
3-Benzoyl-2-isobutyl-5,6-dihydro-4H-cyclopenta[b]thiophene-6-carboxylic acid (a)
3-benzoyl-2-isobutyl-5,6-dihydro-4H-cyclopenta[b]thiophene-6-ethylcarboxylate: ($C_{21}H_{24}O_3S$)

To a suspension of 19.8 g (0.15 mole) of aluminum chloride in 120 cc of methylene chloride were successively added, drop by drop, 9.4 g (0.037 mole) of 2-isobutyl-5,6-dihydro-4H-cyclopenta[b]thiophene-6-ethylcarboxylate, then 9.8 g (0.070 mole) of benzoyl chloride. The reaction mixture was refluxed for 6 hours. After cooling, it was poured into an ice-hydrochloric acid mixture. The organic phase was separated and the aqueous phase extracted with methylene chloride. The organic solutions were collected, washed with water and dried on sodium sulfate. The solvent and excess benzoyl chloride were eliminated by distillation under reduced pressure. The residue was purified by chromatograhy on a silica column (eluant: 4/1 hexane-ethyl acetate). 11.8 g (yield=89%) of 3-benzoyl-2-isobutyl-5,6-dihydro-4H-cyclopenta[b]thiophene-6-ethylcarboxylate was obtained in the form of an oil used in the next stage without further purification. An analytical sample was obtained by distillation, Bp0.9=185° C.

| Analysis in percent | C % | H % | S % |
|---|---|---|---|
| Calculated | 70.75 | 6.79 | 9.00 |
| Found | 70.56 | 6.93 | 8.79 |

IR$\nu$(C=O)=1735 and 1655 cm$^{-1}$.

(b)
3Benzoyl-2-isobutyl-5,6-dihydro-4H-cyclopenta[b]thiophene-6-carboxylic acid: ($C_{19}H_{20}O_3S$)

A solution of 7.7 g (0.073 mole) of sodium carbonate in 300 cc of water was added to a solution of 11.3 g (0.037 mole) of 3-benzoyl-2-isobutyl-5,6-dihydro-4H-cyclopenta[b]thiophene-6-ethylcarboxylate in 85 cc of ethanol. The mixture was refluxed for 1 hour. 4 g of charcoal was added and the reflux was continued for another hour and filtering was performed. The filtrate was evaporated dry. The residue was picked up with water, the solution was washed with ether then acidified with dilute hydrochloric acid. 3-Benzoyl-2-isobutyl-5,6-dihydro-4H-cyclopenta[b]thiophene-6-carboxylic acid precipitated. It was filtered, washed with water, dried and recrystallized in a hexane-ethyl acetate mixture. Yield=7.3 g (61%). Mp=106°–108° C.

| Analysis in percent | C % | H % | S % |
|---|---|---|---|
| Calculated | 69.48 | 6.14 | 9.76 |
| Found | 69.49 | 6.05 | 9.72 |

IR$\nu$(C=O)=1710 and 1635 cm$^{-1}$.

NMR (CDCl$_3$) δ=0.9 (d, 6H); 1.3-2.2 (m, 1H); 2.3-2.9 (complex multiplet, 6H); 3.9-4.3 (m, 1H); 7.3-8.0 (complex multiplet, 5H); 11.0-11.3 (broadened peak, 1H exchangeable by CF3COOD).

EXAMPLE 33

2-isobutyl-3-(2-thenoyl)-5,6-dihydro-4H-cyclopenta[b]-thiophene-6-carboxylic acid (a) Ethyl-2-isobutyl-3-(2-thenoyl)-5,6-dihydro-4H-cyclopenta[b]thiophene-6-carboxylate: (C$_{19}$H$_{22}$O$_3$S$_2$)

By operating as in example 32 starting from 9.4 g (0.037 mole) of 2-isobutyl-5,6-dihydro-4H-cyclopenta[b]thiophene-6-ethylcarboxylate, 19.8 g (0.15 mole) of aluminum chloride and 10.2 g (0.070 mole) of 2-thenoyl chloride, there was obtained after purification on a silica column 12.4 g (yield=92%) of 2-isobutyl-3-(2-thenoyl)-5,6-dihydro-4H-cyclopenta[b]thiophene-6-ethylcarboxylate in the form of an oil used afterwards without further purification. An analytical sample was obtained by distillation. Bp1=160° C.

| Analysis in percent | C % | H % | S % |
| --- | --- | --- | --- |
| Calculated | 62.95 | 6.12 | 17.69 |
| Found | 63.25 | 6.13 | 17.48 |

IR$\nu$(C=O)=1740 and 1640 cm$^{-1}$.

(b) 2-Isobutyl-3-(2-thenoyl)-5,6-dihydro-4H-cyclopenta[b]-thiophene-6-carboxylic acid: (C$_{17}$H$_{18}$O$_3$S$_2$)

By operating as in example 32 starting from 10.9 g (0.033 mole) of the above ester and 6.4 g (0.06 mole) of sodium carbonate, 6.4 g (yield=58%) of the desired acid was obtained. Mp=129°-131° C. (hexane-ethyl acetate).

| Analysis in percent | C % | H % | S % |
| --- | --- | --- | --- |
| Calculated | 61.05 | 5.42 | 19.18 |
| Found | 60.89 | 5.70 | 19.13 |

EXAMPLE 34

(5-ethyl-2-thienyl)succinic acid (a) Diethyl(5-ethyl-2-thienyl)methylene malonate Obtained by operating as in example 28 starting from 194.5 g (1.38 mole) of 5-ethyl-2-thiophenecarboxaldehyde [prepared according to W. J. King and F. K. Noro, J. Org. Chem. 1948, 13, 635] and 318.2 g (2 moles) of ethyl malonate. Yield=372 g (95%). Bp 1.5=155° C.

(b) (5-ethyl-2-thienyl)succinic acid: (C$_{10}$H$_{12}$O$_4$S.)

Obtained by operating as in example 28 starting from 362.2 g (1.28 mole) of diethyl(5-ethyl-2-thienyl)methylene malonate and 163.1 g (2.50 mole) of potassium cyanide. Yield=189.4 g (65%). Mp=165°-166° C. (hexane-ethyl acetate).

| Analysis in percent | C % | H % | S % |
| --- | --- | --- | --- |
| Calculated | 52.61 | 5.30 | 14.05 |
| Found | 52.88 | 5.26 | 13.98 |

Example 35

2-Ethyl-4-oxo-5,6-dihydro-4H-cyclopenta[b]thiophene-6-carboxylic acid (a) (5-ethyl-2-thienyl)succinic anhydride: (C$_{10}$H$_{10}$O$_3$S)

Ring formation of 20 g (0.088 mole) of (5-ethyl-2-thienyl)succinic acid by 90 cc of acetyl chloride, performed under the conditions of example 3, provided 14.4 g (yield=78%) of (5-ethyl-2-thienyl)succinic anhydride.
Bp0.4=145°-148° C.

| Analysis in percent | C % | H % | S % |
| --- | --- | --- | --- |
| Calculated | 57.12 | 4.79 | 15.25 |
| Found | 57.24 | 4.65 | 15.09 |

IR$\nu$(C=O)=1865 and 1790 cm$^{-1}$.

(b) 2-Ethyl-4-oxo-5,6-dihydro-4H-cyclopenta[b]thiophene-6-carboxylic acid: (C$_{10}$H$_{10}$O$_3$S)

Starting from 11.7 g (0.056 mole) of the above anhydride and 20.1 g (0.15 mole) of aluminum chloride, there was obtained, by operating as in example 29 but by heating the reaction medium for 30 minutes at 80° C., 8.8 g (yield 75%) of the desired acid (mp=128°-132° C.) used in the next stage without further purification. An analytical sample was obtained by recrystallization in a hexane-ethyl acetate mixture. Mp=143°-145° C.

| Analysis in percent | C % | H % | S % |
| --- | --- | --- | --- |
| Calculated | 57.12 | 4.79 | 15.25 |
| Found | 57.39 | 4.66 | 15.26 |

IR$\nu$(C=O)=1720 and 1655 cm$^{-1}$.
NMR (CDCl$_3$) δ=1,3 (t, 3H); 2.6-3.4 (m, 4H); 4.3-4.6 (m, 1H); 6.9 (s, 1H); 10.1 (s, 1H, exchangeable by CF3COOD).

EXAMPLE 36

2-Ethyl-5,6-dihydro-4H-cyclopenta[b]thiophene-6-carboxylic acid: (C$_{10}$H$_{12}$O$_2$S)

By operating as in example 5 starting from 10 g (0.048 mole) of 2-ethyl-4-oxo-5,6-dihydro-4H-cyclopenta[b]-thiophene-6-carboxylic acid, 40 g (0.61 g at) of zinc powder and 4 g (0.015 mole) of mercuric chloride, there was obtained 4.7 g (yield=50%) of the desired acid. Mp=81°-82° C. (hexane-ethyl acetate).

| Analysis in percent | C % | H % | S % |
| --- | --- | --- | --- |
| Calculated | 61.19 | 6.17 | 16.34 |
| Found | 60.86 | 6.23 | 16.15 |

IR$\nu$(C=O)=1700 cm$^{-1}$.
NMR (CDCl$_3$) δ=1.3 (t, 3H); 2.5-3.3 (m, 6H); 3.9-4.4 (m, 1H); 6.6 (s, 1H); 10.8-11.1 (broadened peak, 1H exchangeable by CF3COOD).

EXAMPLE 37

2-ethyl-5,6-dihydro-4H-cyclopenta[b]thiophene-6-ethylcarboxylate: (C$_{12}$H$_{16}$O$_2$S)

Esterification of 40 g (0.20 mole) of 2-ethyl-5,6-dihydro-4H-cyclopenta[b]thiophene-6-carboxylic acid performed under the conditions of example 6 provided the desired ester. The raw product was purified by chromatography on a silica column (4/1 hexane-ethyl acetate eluant). It was used in the next stage without further purification. Yield=39.9 g (89%). An analytical sample was obtained by distillation. Bp0.6=98°-101° C.

| Analysis in percent | C % | H % | S % |
|---|---|---|---|
| Calculated | 64.25 | 7.19 | 14.29 |
| Found | 63.98 | 7.05 | 14.01 |

IR$\nu$(C=O)=1740 cm$^{-1}$.

EXAMPLE 38

3-Benzoyl-2-ethyl-5,6-dihydro-4H-cyclopenta[b]thiophene-6-carboxylic acid (a)

3-benzoyl-2-ethyl-5,6-dihydro-4H-cyclopenta[b]thiophene-6-ethylcarboxylate: ($C_{19}H_{20}O_3S$)

By operating as in example 32 starting from 5 g (0.022 mole) of 2-ethyl-5,6-dihydro-4H-cyclopenta[b]thiophene-6-ethylcarboxylate, 6.1 g (0.043 mole) of benzoyl chloride and 12.2 g (0.092 mole) of aluminum chloride, there was obtained after purification on a silica column (4/1 hexane-ethyl acetate eluant) 4.9 g (yield=68%) of the desired ester. An analytical sample was obtained by distillation. Bp2=172°-176° C.

| Analysis in percent | C % | H % | S % |
|---|---|---|---|
| Calculated | 69.48 | 6.14 | 9.76 |
| Found | 69.24 | 6.11 | 9.54 |

IR$\nu$(C=O)=1740 and 1650 cm$^{-1}$.

(b)

3-Benzoyl-2-ethyl-5,6-dihydro-4H-cyclopenta[b]thiophene-6-carboxylic acid: ($C_{17}H_{16}O_3S$)

Saponification of 14.9 g (0.046 mole) of the above ester under the conditions described in example 32 provided 5 g (yield=36%) of the desired acid. Mp=123°-124° C. (cyclohexane).

| Analysis in percent | C % | H % | S % |
|---|---|---|---|
| Calculated | 67.97 | 5.37 | 10.67 |
| Found | 68.10 | 5.49 | 10.52 |

IR$\nu$(C=O)=1695 and 1640 cm$^{-1}$.

NMR (CDCl$_3$) $\delta$=1.3 (t, 3H); 2.5-3.2 (m, 6H); 3.9-4.3 (complex multiplet, 1H); 7.3-8.0 (m, 5H); 10.5 (broadened peak, 1H exchangeable by CF3COOD).

EXAMPLE 39

3(4-Chlorobenzoyl)-2-ethyl-5,6-dihydro4H-cyclopenta[b]thiophene-6-carboxylic acid: ($C_{17}H_{15}ClO_3S$)

By operating as in example 32 starting from 6.6 g (0.029 mole) of 2-ethyl-5,6-dihydro-4H-cyclopenta[b]thiophene-6-ethylcarboxylate, 9.6 g (0.055 mole) of 4-chlorobenzoyl chloride and 15.8 g (0.118 mole) of aluminum chloride, there was obtained, after filtration on a silica column (4/1 hexane-ethyl acetate eluant) then distillation, 9.4 g (yield=89%) of 3-(4-chlorobenzoyl)-2-ethyl-5,6-dihydro-4H-cyclopenta[b]thiophene-6-ethylcarboxylate. Bp0.7=196-200 C. Saponification of this ester under the conditions described in example 32 provided 4.5 g (yield=52%) of the desired acid. Mp=136°-138° C. (hexane-ethyl acetate).

| Analysis in percent | C % | H % | Cl % | S % |
|---|---|---|---|---|
| Calculated | 60.98 | 4.52 | 10.59 | 9.58 |
| Found | 61.01 | 4.48 | 10.89 | 9.64 |

EXAMPLE 40

2-Ethyl-3-(2-thenoyl)-5,6-dihydro-4H-cyclopenta[b]thiophene-6-carboxylic acid: ($C_{15}H_{14}O_3S_2$)

By operating as in example 32 starting from 15 g (0.067 mole) of 2-ethyl-5,6-dihydro-4H-cyclopenta[b]thiophene-6-ethylcarboxylate, 14.6 g (0.1 mole) of 2-thenoyl chloride and 35.8 g (0.268 mole) of aluminum chloride, there was obtained, after filtration on a silica column then distillation, 17.2 g (yield=77%) of 2-ethyl-3-(2-thenoyl)-5,6-dihydro-4H-cyclopenta[b]thiophene-6-ethylcarboxylate. Bp0.8=188°-192° C. Saponification of 5.7 g of this ester under the conditions described in example 32 provided 2.5 g (yield=48%) of the desired acid. Mp=82°-85° C.) (hexane-benzene).

| Analysis in percent | C % | H % | S % |
|---|---|---|---|
| Calculated | 58.80 | 4.60 | 20.93 |
| Found | 58.65 | 4.48 | 21.19 |

EXAMPLE 41

3-Benzoyl-2-methyl-5,6-dihydro-4H-cyclopenta[b]thiophene-6-carboxamide: ($C_{16}H_{15}NO_2S$)

5.6 g (0.047 mole) of thionyl chloride was added to a mixture of 5.4 g (0.019 mole) of 3-benzoyl-2-methyl-5,6-dihydro-4H-cyclopenta[b]thiophene-6-carboxylic acid and 80 cc of benzene. The mixture was refluxed for 2 hours then concentrated dry under reduced pressure. The residue was dissolved in 100 cc of benzene. The solution was cooled to 15° C. and treated with an ammonia current for 20 minutes. The resulting precipitate was filtered, washed with water and dried. After recrystallization in ethyl acetate there was obtained 3.7 g (yield=68%) 3-benzoyl-2-methyl-5,6-dihydro-4H-cyclopenta[b]thiophene-6-carboxamide. Mp=165°-168° C.

| Analysis in percent | C % | H % | N % | S % |
|---|---|---|---|---|
| Calculated | 67.34 | 5.30 | 4.91 | 11.24 |
| Found | 67.52 | 5.08 | 4.90 | 10.95 |

IR$\nu$(C=O)=1660 and 1650 cm$^{-1}$.

EXAMPLE 42

Methyl-3-benzoyl-5,6-dihydro-4H-cyclopenta[b]thiophene-6-carboxylate: ($C_{17}H_{16}O_3S$)

A slight bubbling of hydrochloric gas was maintained for 8 hours in a refluxed solution of 17.7 g (0.062 mole) of 3-benzoyl-2-methyl-5,6-dihydro-4H-cyclopenta[b]thiophene-6-carboxylic acid in 300 cc of methanol. The solvent was evaporated under reduced pressure and the residue was picked up with water and extracted with ether. The ether solution was washed with a sodium carbonate solution then with water and dried on sodium sulfate. After elimination of the solvent, the residue was recrystallized in a hexane-ethyl acetate mixture. Yield=9 g (48%). Mp=78°-80° C.

| Analysis in percent | C % | H % | S % |
|---|---|---|---|
| Calculated | 67.97 | 5.37 | 10.68 |
| Found | 67.71 | 5.32 | 10.85 |

IR$\nu$(C=O)=1740 and 1660 cm$^{-1}$.

EXAMPLE 43

3-benzoyl-2-methyl-5,6-dihydro-4H-cyclopenta[b]thiophene-6-(2-diethylamino)ethylcarboxylate, oxalate: ($C_{24}H_{29}NO_7S$)

A mixture of 6.9 g (0.024 mole) of 3-benzoyl-2-methyl-5,6-dihydro-4H-cyclopenta[b]thiophene-6-carboxylic acid, 8.3 g (0.048 mole) of 2-diethylaminochlorothane hydrochloride, 7.9 g (0.057 mole) of potassium carbonate and 100 cc of acetone was refluxed for 16 hours. After cooling, the reaction mixture was filtered. The filtrate was concentrated dry under reduced pressure. The residue was picked up by 0.1N hydrochloric acid and extracted with ether. The aqueous phase was separated and made basic by 4N sodium hydroxide. The oil that separated was extracted with ether. The ether solution was washed with water, dried on sodium sulfate and concentrated dry. Distillation of the residue provided 6.3 g (yield=68%) of 2-(diethylamino)ethyl-3-benzoyl-2-methyl-5,6-dihydro-4H-cyclopenta[b]thiophene-6-carboxylate (Bp0.6=205°-208° C.). The oxalate was prepared as follows: a solution of 4.9 g of base in 15 cc of acetone was treated with a solution of 1.5 g of oxalic acid in 20 cc of acetone. The oxalate precipitate was filtered and recrystallized in an isopropanol-ethyl acetate mixture. Mp=93°-95° C.

| Analysis in percent | C % | H % | N % | S % |
|---|---|---|---|---|
| Calculated | 60.61 | 6.15 | 2.94 | 6.74 |
| Found | 60.50 | 6.08 | 2.96 | 6.98 |

It is to be understood that the present invention is not limited to the embodiments disclosed which are illustratively offered and that modifications may be made without departing from the invention.

What is claimed is:

1. A 5,6-dihydro-4H-cyclopenta[b]thiophene-6-carboxylic acids of the formula

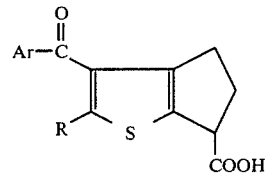

in which Ar is phenyl, optionally substituted by one or more halogen atoms or by a lower alkyl, lower alkoxy, hydroxy, nitro or dimethylamino group; thienyl optionally substituted by a halogen atom or a lower alkyl group; or furyl group R is methyl or ethyl; a pharmaceutically acceptable salt, or ester or amide thereof.

2. 5,6-Dihydro-4H-cyclopenta[b]thiophene-6-carboxylic acid according to claim 1, wherein R is methyl, or a pharmaceutically acceptable salt ester or amide thereof.

3. 2-Methyl-3-(2-thenoyl)-5,6-dihydro-4H-cyclopenta[b]thiophene-6-carboxylic acid according to claim 1, or a pharmaceutically acceptable salt, ester or amide thereof.

4. 3-(4-Fluorobenzoyl)-2-methyl-5,6-dihydro-4H-cyclopenta[b]thiophene-6-carboxylic acid according to claim 1, or a pharmaceutically acceptable salt, ester or amide thereof.

5. 3-(4-Dimethylaminobenzoyl)-2-methyl-5,6-dihydro-4H-cyclopenta[b]thiophene-6-carboxylic acid according to claim 1, or a pharmaceutically acceptable salt, ester or amide thereof.

6. 3-Benzoyl-2methyl-5,6-dihydro-4H-cyclopenta[b]thiophene-6-carboxylic acid according to claim 1, a pharmaceutically acceptable salt, ester or amide thereof.

7. A medicinal composition containing as active agent an anti-inflammatory or analgesic effective amount of a 5,6-dihydro-4H-cyclopenta[b]thiophene-6-carboxylic acid, according to claim 1 or a pharmaceutically acceptable salt, ester or amide thereof, together with a pharmaceutically acceptable excipient.

8. Composition according to claim 7 containing as active agent 2-methyl-3-(2-thenoyl)-5,6-dihydro-4H-cyclopenta[b]thiophene-6-carboxylic acid, or a pharmaceutically acceptable salt, ester or amide thereof.

9. Composition according to claim 7 containing as active agent 3-(4-fluorobenzoyl)-2-methyl-5,6-dihydro-4H-cyclopenta[b]thiophene-6-carboxylic acid, or a pharmaceutically acceptable salt, ester or amide thereof.

10. Composition according to claim 7 containing as active agent 3-(4-dimethylaminobenzoyl)-2-methyl-5,6-dihydro-4H-cyclopenta[b]thiophene-6-carboxylic acid, or a pharmaceutically acceptable salt, ester or amide thereof.

11. Composition according to claim 7 containing as active agent 3-benzoyl-2-methyl-5,6-dihydro-4H-cyclopenta[b]thiophene-6-carboxylic acid, or a pharmaceutically acceptable salt, ester or amide thereof.

* * * * *